United States Patent [19]

Richez

[11] Patent Number: 4,605,415

[45] Date of Patent: Aug. 12, 1986

[54] BIOREACTIVE MATERIALS

[75] Inventor: Raymond M. Richez, Mons, Belgium

[73] Assignee: Region Wallonne, representee par l'Executif Regional Wallon, Brussels, Belgium

[21] Appl. No.: 557,495

[22] Filed: Dec. 2, 1983

[30] Foreign Application Priority Data

Dec. 2, 1982 [BE] Belgium ................ 895229

[51] Int. Cl.[4] ................ A61F 2/28; C03C 3/097
[52] U.S. Cl. ................ 623/16; 623/66; 501/63; 501/73
[58] Field of Search ................ 3/1, 1.9; 427/2; 501/55, 57, 58, 59, 63, 64, 73, 77

[56] References Cited

U.S. PATENT DOCUMENTS

| | | | |
|---|---|---|---|
| 3,922,155 | 11/1975 | Broemer et al. | 501/63 X |
| 4,120,730 | 11/1978 | Trojer et al. | 501/73 X |
| 4,159,358 | 6/1979 | Hench et al. | 128/92 CA X |
| 4,234,972 | 11/1980 | Hench et al. | 3/1.9 |
| 4,560,666 | 12/1985 | Yoshida et al. | 501/77 X |

Primary Examiner—Richard J. Apley
Assistant Examiner—Alan W. Cannon
Attorney, Agent, or Firm—Sughrue, Mion, Zinn, Macpeak and Seas

[57] ABSTRACT

Bioreactive materials, for use in forming implants or prostheses, obtained by fusion of a mixture of 20 to 50% by weight of $SiO_2$, 15 to 25% by weight of CaO, 5 to 10% by weight of $P_2O_5$, 15 to 25% by weight of $Na_2O$ and 3 to 15% by weight of $Al_2O_3$, or their metallic precursors yielding equivalent quantities of oxides by fusion.

7 Claims, No Drawings

BIOREACTIVE MATERIALS

BACKGROUND OF THE INVENTION

The present invention relates to new bioreactive materials used in particular for implants and prostheses on man or animals in the medical, dental and veterinarian fields.

Bioreactive materials, in accordance with the present invention, means materials resulting from the fusion of mixtures of oxides or salts or any other metallic precursor, such materials being capable of reacting biochemically with living tissues and in particular with osseous tissues.

Biologically active glasses and vitroceramics have been known for many years. Compositions containing from 40 to 60% of $SiO_2$ and $B_2O_3$, 25% of $Na_2O$, 25% of CaO and a few percent of $P_2O_5$ have been the subject of numerous experiments. In the case of such compositions, fastening to the bone is dependent upon the formation on the surface of the material of a microporous structure developing a large specific surface, for example a silica gel, protected by a layer which is rich in Ca and P ions. The selective diffusion of the sodium, calcium and phosphorous ions and the partial dissolution of the lattice of the material are the principal steps which lead to this superficial structure causing mineralization of the bone at its surface.

According to U.S. Pat. Nos. 2,301,488 and 2,243,915, materials formed from a vitreous phase and a crystalline phase such as hydroxyapatite or other compounds of the same crystalline group are based on the principle according to which the presence of hexagonal crystalline phases in the vitreous phase assists the epitaxial growth of the apatite in the material.

In accordance with the prior art the same reactive principle on the surface of the material in contact with the living tissues always leads to the formation of a medium developing a large specific surface, such as for example a silica gel.

These various materials have an osteogenic property when they are in contact with a physiological medium. Nevertheless, experiments conducted on sheep, the results of which are given in *J. of Biomedic. Mater. Res.*, Vol. 12, 57–65 (1978), have shown that the superficial structure developed by conventional materials do not provide long-term mechanical holding for the implants they coat. In a corrosive medium, such as the physiological medium, this superficial structure destroys itself and causes too much corrosion of the implant.

SUMMARY OF THE INVENTION

An object of the present invention is to overcome these disadvantages by acting on the surface reactivity of the material so as to increase the corrosion resistance of the superficial layers. Consequently their long-term mechanical resistance is improved whilst retaining the same osteogenic properties as the materials known to date.

The present invention provides new bioreactive materials which develop on their surface, on contact with living tissues, a silico-aluminous layer which is formed after selective dissolution of ions in the surrounding medium. Such bioreactive materials which have never been synthesized until now are obtained by the selection in defined proportions of the various metallic oxides which constitute them.

The bioreactive materials in accordance with the present invention are characterized in that they are obtained by fusion of a mixture of 20 to 50% by weight of $SiO_2$, 15 to 25% by weight of CaO, 5 to 10% by weight of $P_2O_5$, 15 to 25% by weight of $Na_2O$ and 3 to 15% by weight of $Al_2O_3$ or of their metallic precursors yielding equivalent quantities of oxides by fusion.

DETAILED DESCRIPTION OF THE INVENTION

Fusion is used to mean any process which, at a temperature greater than 500° C., enables a vitreous structure to be obtained. The mixture before fusion can be obtained by known techniques, such as, for example, the mixture of powders, or by indirect techniques, such as, for example, the gel method.

Metallic precursor is used to mean any metallic compound capable of yielding oxides by fusion. For example, hydroxides, carbonates and nitrates can be used in accordance with the present invention in equivalent quantities such that the desired quantities of oxides are obtained by fusion.

The bioreactive compositions which are the object of the present invention must always contain a minimum quantity of lattice-forming ions, $SiO_2$ and $Al_2O_3$, which guarantee the formation on contact with osseous tissues of a silico-aluminous layer and the long-term chemical stability of the material.

The $SiO_2$ content must be greater than 20% since it is the principal lattice-forming ion of glass. An $SiO_2$ content of greater than 50% greatly diminishes the reactivity of the bioreactive material.

The presence of aluminum oxide reinforces the corrosion resistance of the surface structures of the bioreactive material. It has been noted that $Al_2O_3$ must be present in a quantity of at least approximately 3% by weight in order to fulfill this role. A high alumina content of over 15% by weight causes a series of phenomena which are difficult to control during preparation, in particular devitrification which modifies the properties of the bioreactive materials.

The quantities of $P_2O_5$ used in the compositions to obtain the bioreactive materials are between 5 and 10% by weight. This element assists in the formation of the bone at the surface of the material but an increase of the upper limit brings about no particular advantage.

The alkaline and alkaline earth ion contents determine the short term and medium term reactivities of the material. These contents must therefore be carefully selected dependent upon the various parameters of use, such as, for example, vascularization of the physiological medium. They are between 15 and 25% by weight of each of CaO and $Na_2O$. The CaO may be substituted with MgO and/or $CaF_2$ and the $Na_2O$ may be substituted with $K_2O$ and/or $Li_2O$.

In vivo experiments have shown that the presence of CaO and $P_2O_5$ in the bioreactive materials assists osseous regrowth on the surface of same. Moreover, the ratio of the CaO and $P_2O_5$ contents is selected such that this phenomenon is optimal. Preferably this ratio is 3.

In accordance with the present invention, the new bioreactive material compositions can additionally include 5 to 25% by weight of $B_2O_3$. This percentage of $B_2O_3$ can be adjusted so as to decrease the fusion temperature of the assembly of compounds and to facilitate the process for preparation of the material.

It should be noted that the addition of $B_2O_3$ has an influence on the physiological characteristics of the final material. Dependent upon the uses envisaged, physical characteristics such as the thermal expansion coefficient and the evolution of the viscosity as a function of the temperature can be adjusted by varying the quantity of $B_2O_3$ in the material within the limits claimed.

The silico-aluminous layer which is formed in the presence of living tissues constitutes a medium which possesses particularly interesting catalytic properties. In addition, it has much higher corrosion resistance in an alkaline medium than silica gel. In this manner it is possible to more easily control the long term behavior of this material.

Experiments have shown that this silico-aluminous layer was stable in media having a pH of 11, and that under such conditions it was not necessary for it to be protected with a Ca-P layer in order to keep a constant thickness. This fact is an illustration of the beneficial effect of the addition of $Al^{3+}$ ions in a silicated lattice on the corrosion of same.

In accordance with a preferred embodiment of the invention, the bioreactive materials are obtained by fusion of a mixture of 25 to 35% by weight of $SiO_2$, 15 to 25% by weight of CaO, 5 to 10% by weight of $P_2O_5$, 15 to 25% by weight of $Na_2O$, 5 to 12% by weight of $Al_2O_3$ and 10 to 20% by weight of $B_2O_3$ or of their metallic precursors yielding equivalent quantities of oxides by fusion.

Other metallic oxides can possibly be present in the raw materials or can be added to the raw materials in small quantities without departing from the framework of the present invention. Such oxides have a negligible effect on the properties of the final material.

The new bioreactive materials which are the object of the present invention are obtained by fusion such as defined above or by any other similar known method. For example, by the powder method, the fusion can be carried out at temperatures of between 1,100° and 1,450° C. for periods of from 3 to 12 hours. By the gel method, the fusion can be carried out at much lower temperatures, for example slightly above 500° C. In accordance with the first method, the components are for example premixed in a rotary jar for a few hours before undergoing the fusion treatment. The melted mixture is either poured into graphite molds of the desired shape in which the product is reheated, or cast and ground for example into powder or into particles of the desired granular size.

Any other fusion, molding, casting or injection technique can be used for the production of bioreactive materials. The new bioreactive materials have numerous applications in particular in the medical, dental and veterinarian fields.

The bioreactive materials of the present invention are used as a base or coating material. Base material is used also to mean any composition obtained based upon the bioreactive materials which are the object of the present invention and upon other materials, charges and/or additives; these latter compounds can be ceramic powders such as, for example, alumina or hydroxyapatite. The base materials can be in various forms, for example in the form of powders, particles, flakes and fibers. They can be used for the production of finished products of the most varied types: for example, shaped products of any shape whatsoever, fabrics, knits or non-woven materials with applications in the medical, dental and veterinarian fields.

By using known techniques, for example casting and molding, any implant or prosthesis can be produced from these new bioreactive materials.

The bioreactive materials of the present invention are also used as a coating or covering material for implants and/or prostheses. Such may be partially or totally coated. They lend themselves particularly well to the coating of aluminum oxide ceramic parts without fear of diffusion of the $Al^{3+}$ ions during deposition and they can also be used for the coating or covering of parts composed of other ceramics, metals or glasses. For this type of application, any known coating technique may be used, for example plasma spraying.

The new bioreactive materials claimed have a particularly interesting application in the fixation of hip prostheses. By use of these bioreactive materials, it is possible, by using forms of self-blocking prostheses, to fix them without use of cement and thus to obtain a biologically ideal cementing since these bioreactive materials participate in the regrowth of osseous tissue and in the bonding of same.

The new bioreactive materials can also have many applications in medical fields other than orthopedic ones. By way of example, the replacement of small bones in the internal middle ear may be cited.

In the dental field, the bioreactive materials may be used as components for implants for fixing dental crowns.

In the veterinary field, they can be used, for example, to produce orthopedic prostheses for dogs and horses.

When they are implanted in a living medium, these bioreactive materials undergo on their surface a sequence of selective chemical diffusions which lead to the formation of a medium favorable to osseous regrowth.

This reactivity in a physiological medium leads to the formation of a durable chemical bond which is mechanically stable with the surrounding bones. For this reason, these materials are in particular intended for the fixing of prostheses and implants which are in contact with bones or with a physiological medium in which osteogenesis is possible.

The present invention will be understood more clearly from the following non-limitative examples:

EXAMPLE 1

A bioreactive material was obtained by fusion at 1350° C. for 3 hours of a mixture of 21% by weight of $SiO_2$, 24.5% by weight of each of CaO and $Na_2O$, 6% by weight of $P_2O_5$, 9% by weight of $Al_2O$ and 15% by weight of $B_2O_3$ A conventional known composition comprising 30% by weight of $SiO_2$, 15% by weight of $B_2O_3$, 24.5% by weight of each of $Na_2O$ and CaO and 6% by weight of $P_2O_5$, but not containing $Al_2O_3$ was used as a comparative composition.

The advantages of the present invention were demonstrated by subjecting the new material to in vitro and in vivo corrosion tests.

Part of the in vitro tests were conducted on powders of from 44 $\mu$m to 104 $\mu$m obtained by grinding the cast mass and sieving, wherein the granulometric distribution was controlled by sedigraphy. Another part of the in vitro tests was conducted on parallelepipedal plates which were previously cut and polished with a diamond tool. The test consisted of exposing the powders and the plates to a buffered aqueous solution with a pH of 7.2 and a non-buffered solution (demineralized water) for times varying from 1 day to 8 weeks.

The evolution of the crystalline phases was followed by diffraction of X-rays; chemical analyses were conducted by plasma spectrophotometry on the powders and analysis of the concentration profiles of the various elements at the surface of the plates was carried out by means of an electronic microprobe. The specific evolution of the surface of the powders was able to be followed by a method of nitrogen adsorption.

The study of the in vitro kinetics of the conventional composition used for comparison purposes and of the new composition claimed enabled the fundamental differences between the surface behavior of these two materials to be shown:

The surface reactivity of the new bioreactive material is greater than that of the conventional composition (faster diffusion of the $Ca^{++}$, $Na^+$ modifying ions).

In a first phase, the aluminum oxide participates in the formation of the vitreous phase lattice of the bioreactive material.

The leaching of the $Ca^{++}$ and $Na^+$ surface ions of the new material leads to the formation of a silico-aluminous gel developing a specific surface of several $m^2/g$ which is particularly resistant to alkaline corrosion. This silico-aluminous surface layer itself forms a protection which, by its presence, blocks the diffusion phenomena of the modifying ions.

On the other hand, the in vivo tests described below show that the new material, through simple mechanisms, produces a remarkable chemical bond with the osseous tissues with which it is in contact.

Implants were prepared using the various oxides or various carbonates corresponding to the composition given above by fusion at temperatures of 1350° C. for 3 hours and by pouring into parallelepipedal graphite molds.

The components thus obtained were cut so as to obtain implants like those tested in vitro. The implants were polished on a diamond wheel and sterilized with ethylene dioxide. The implants were then placed in 150 g male Sprague Dawley rats. The animal was anesthetized. On the interior surface of the rear left leg the tibia was freed from the surrounding muscles, a slit was made through the lateral cortex using an electric drill and the implant was inserted into the slit. The incision was closed with stitches and staples. Fixing to the bone was evaluated after 30 days of implantation. The tibias were removed from the dead animals and the adherent tissues were removed therefrom. The zone close to the implant was examined both by histological sections produced after removal of the implant from the receiving bone and by electronic microprobe after lyophilization. The examination of the implants extracted from the dead animal after 1 month showed that the incision made in the tibia was completely filled with mineralized bone and that the osseous growths on the implant fixed the implant in a perfect manner.

Analyses through the cortical-implant interface clearly showed the silico-aluminous barrier formed at the surface of the new material, that this barrier was permeable to collagen macromolecules and muccopolysaccharides and acted as a catalytic medium for the mineralization of the bone.

The same experiments were carried out on a conventional composition. The results showed clearly that, in the majority of cases, these materials underwent a sequence of corrosion which, in the medium term, led to the total destruction of the material.

EXAMPLE 2

Implants were made from an alloy of titanium covered with the bioreactive material for which the composition is given in Example 1.

Powders with a granule size of between 60 and 100 $\mu m$ were synthesized in order to cover the implants with a 300 $\mu m$ layer.

The same in vitro and in vivo tests as in Example 1 were applied on the implants covered with the bioreactive material.

The results obtained were comparable to those of Example 1 and the same conclusions on the osteogenic qualities and the corrosion resistance of the bioreactive material were able to be drawn therefrom.

What is claimed is:

1. A vitreous anti corrosive bioreactive material consisting essentially of a mixture of 20 to 50% by weight of $SiO_2$, 15 to 25% by weight of CaO, 5 to 10% by weight of $P_2O_5$, 15 to 25% by weight of $Na_2O$ and 3 to 15% by weight of $Al_2O_3$, formed from a mixture of oxides or their metallic precursors yielding equivalent quantities of oxides by fusion, said material forming a silico-aluminous layer of high corrosion resistance in the presence of living tissues.

2. The bioreactive materials of claim 1, wherein the CaO can be substituted in part with a material selected from the group consisting of MgO, $CaF_2$ and mixtures thereof, and the $Na_2O$ can be substituted in part with a material selected from the group consisting of $K_2O$, $Li_2O$ and mixtures thereof.

3. The bioreactive materials of claim 1, which in addition contain 5 to 25% by weight of $B_2O_3$.

4. The bioreactive materials of claim 2, which in addition contain 5 to 25% by weight of $B_2O_3$.

5. The bioreactive materials of claim 1, formed of a mixture of 25 to 35% by weight of $SiO_2$, 15 to 25% by weight of CaO, 5 to 10% weight of $P_2O_5$, 15 to 25% by weight of $Na_2O$, 5 to 12% by weight of $Al_2O_3$ and 5 to 25% by weight of $B_2O_3$, or their metallic precursors yielding equivalent quantities of oxides by fusion.

6. The bioreactive materials of claim 2, formed of a mixture of 25 to 35% by weight of $SiO_2$, 15 to 25% by weight of CaO, 5 to 10% weight of $P_2O_5$, 15 to 25% by weight of $Na_2O$, 5 to 12% by weight of $Al_2O_3$ and 5 to 25% by weight of $B_2O_3$, or their metallic precursors yielding equivalent quatilities of oxides by fusion.

7. An implant or prosthesis for use in the medical, dental or veterinarian fields comprising a base or coating of the bioreactive material of any of claims 1 to 6.

* * * * *